US00PP21108P3

(12) United States Plant Patent

Wenzel et al.

(10) Patent No.: US PP21,108 P3

(45) Date of Patent: Jun. 29, 2010

(54) *VERBENA* PLANT NAMED 'RADVERB'

(50) Latin Name: *Verbena hybrida*
Varietal Denomination: Radverb

(75) Inventors: Bernard R. Wenzel, Wauwatosa, WI (US); William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 48 days.

(21) Appl. No.: 12/232,234

(22) Filed: Sep. 12, 2008

(65) Prior Publication Data

US 2010/0071103 P1 Mar. 18, 2010

(51) Int. Cl.
*A01H 5/00* (2006.01)

(52) U.S. Cl. ..... Plt./308

(58) Field of Classification Search ..... Plt./308
See application file for complete search history.

(56) References Cited

U.S. PATENT DOCUMENTS

PP15,672 P2 * 3/2005 Sakazaki ..... Plt./308
PP15,742 P2 * 5/2005 Hanes ..... Plt./308

* cited by examiner

*Primary Examiner*—Wendy C Haas
(74) *Attorney, Agent, or Firm*—Buchanan Ingersoll & Rooney PC

(57) ABSTRACT

A new and distinct *Verbena* plant is provided that is a newly found seedling of unknown parentage. Over an extended period of time attractive fragrant blossoms that are purple in coloration are produced. The growth habit is moderately vigorous and trailing and spreading. Attractive medium green foliage is formed that contrasts nicely with the blossom coloration. The plant has been found to be hardy to U.S.D.A. Hardiness Zone No. 6 and also is hardy in Zone No. 5 with the use of protection. The plant can be grown to advantage to provide attractive ornamentation in parks and gardens.

1 Drawing Sheet

Figure 1:
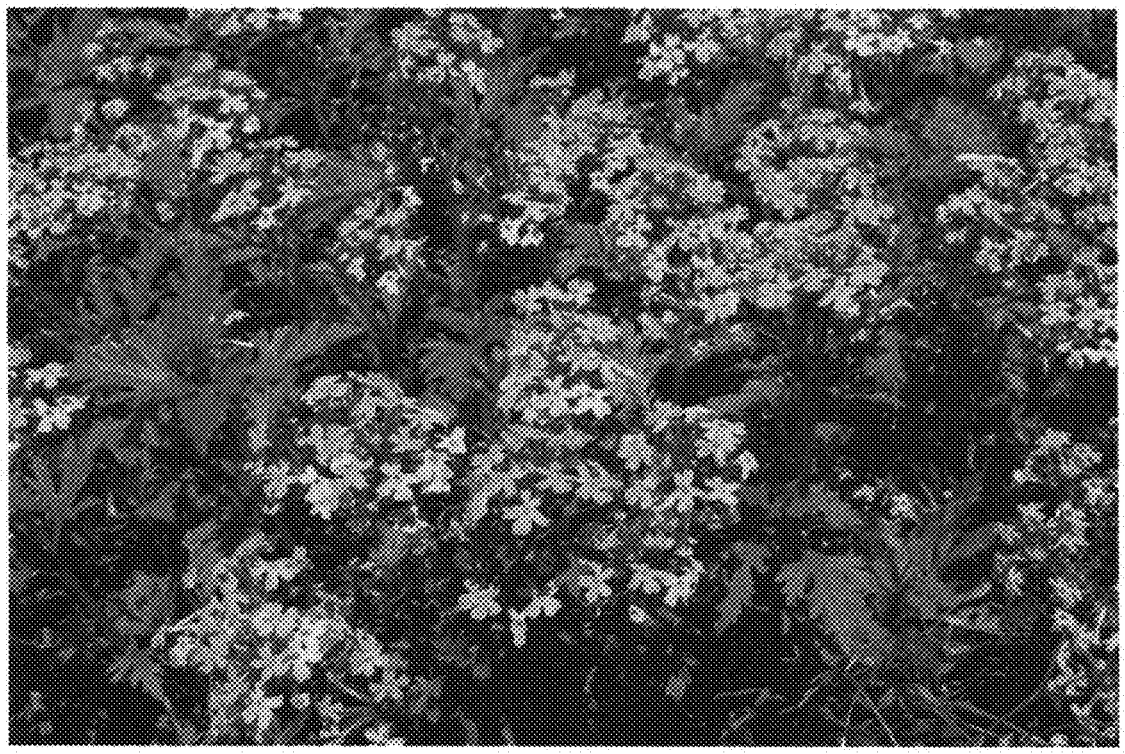

Botanical/commercial classification: *Verbena hybrida/ Verbena* Plant.

Varietal denomination: cv. Radverb.

SUMMARY OF THE INVENTION

A new and distinct highly ornamental perennial *Verbena* cultivar is provided.

During 1995 an unusual *Verbena* plant of unknown parentage was discovered while growing in a residential setting at Rockford, Ill., U.S.A. An open-pollinated progeny of this plant was transplanted to a growing site at Greenfield, Wis., U.S.A. The new cultivar of the present invention is a selection of open-pollinated progeny of the plant being grown at Greenfield, Wis., U.S.A. The new cultivar was selected primarily in view of the appearance of the blossoms, foliage, and the manifest superior hardiness. Had the single plant of the new cultivar not been discovered and preserved it would have been lost to mankind. The new cultivar further has been grown and evaluated near West Grove, Pa., U.S.A.

It was found that the new perennial *Verbena* plant displays the following combination of characteristics:

(a) forms in abundance over an extended period of time attractive fragrant blossoms that are purple in coloration, (b) exhibits a moderately vigorous trailing and spreading growth habit, (c) forms attractive medium green foliage that contrasts nicely with the blossom coloration, (d) displays good cold hardiness, and (e) is well suited for growing as attractive ornamentation.

The new cultivar is commonly substantially continuously flowering from spring to fall when grown outdoors, and commonly blossoms throughout the year under greenhouse growing conditions.

The new cultivar can be distinguished from all other *Verbena* plants of which we are aware. More specifically, the new cultivar can be readily distinguished from the 'Homestead Purple' cultivar (non-patented in the United States) in view of, inter alia, the display by the new cultivar of slightly smaller flowers, a smoother leaf texture, more flower fragrance, and greater hardiness during observations to date.

The new cultivar well meets the needs of the horticultural industry and can be grown to advantage as attractive ornamentation in parks, gardens, public areas, and residential landscapes.

The new cultivar has been asexually reproduced by the rooting of cuttings. Such asexual reproduction as performed at Greenfield, Wis., U.S.A. and near West Grove, Pa., U.S.A. has demonstrated that the characteristics of the new cultivar are firmly fixed and stable and are strictly transmissible from one generation to another. The new cultivar asexually reproduces in a true-to-type manner from one generation to another.

The new cultivar has been named 'Radverb', and will be marketed in the United States under the SWEET THING trademark.

BRIEF DESCRIPTION OF THE PHOTOGRAPH

The accompanying photograph shows as nearly true as it is reasonably possible to make the same in a color illustration of this character a typical specimen of the new cultivar while growing outdoors during the month of May near West Grove, Pa., U.S.A.

FIG. 1 shows a profusion of the attractive purple blossoms in various stages of development as well as the medium green foliage.

DETAILED DESCRIPTION

The chart used in the identification of colors is that of The Royal Horticultural Society (R.H.S. Colour Chart—2001 Edition), London, England. Color terminology in common terms sometimes is included as an aid to the reader. Such color terminology is to be accorded its customary dictionary significance. The description is based on the observation of typical specimens of the new cultivar during the month of August while growing outdoors in containers near West Grove, Pa., U.S.A. Such specimens had been asexually reproduced by the rooting of cuttings.

Plant:

*Form.*—Moderately vigorous, trailing and spreading.

*Growth habit.*—Perennial.

*Height.*—Approximately 24 cm on average.

*Width.*—Approximately 50 cm on average.

*Strength.*—Relatively strong.

*Branch length.*—Commonly approximately 25 cm on average.

*Branch number.*—Commonly approximately 18 main branches on average.

*Branch cross-section.*—Commonly somewhat square.

*Branch thickness.*—Commonly approximately 3 mm on average.

*Branch texture.*—Pubescent.

*Central internode length.*—Commonly approximately 3.5 cm on average.

*Stem color.*—Commonly Yellow-Green Group 145A to Yellow-Green Group 146D when immature and mature.

Foliage:

*Arrangement.*—Opposite.

*Shape.*—Lanceolate.

*Margin.*—Incised.

*Apex.*—Acute.

*Base.*—Aequilateral.

*Venation.*—Reticulate or net-veined.

*Leaf length.*—Commonly approximately 4 cm on average.

*Leaf width.*—Commonly approximately 2 cm on average.

*Leaf texture.*—Upper surface: smooth with a few pubescent hairs. Under surface: coarse with elevated venation and pubescent hairs.

*Leaf quantity.*—Commonly approximately 20 leaves on average per stem.

*Color.*—Upper surface: Green Group 137A to Yellow-Green 143A when young and mature. Lower surface: Yellow-Green Group 146D to Yellow-Green Group 147C when young and mature.

*Fragrance.*—Earthy scent.

*Lastingness.*—The blossoms commonly last approximately 5 to 7 days on the plant.

*Petiole.*—Commonly approximately 2.5 cm in length, approximately 2 mm in diameter, lightly coarse with the presence of hirsute hairs, and Green Group 143C in coloration.

Inflorescence:

*Type.*—Corymb, sessile, salverform.

*Length.*—Commonly approximately 2 cm on average.

*Width.*—Commonly approximately 4 cm on average.

*Number.*—Commonly approximately 20 to 30 per plant.

*Flowers per inflorescence.*—Commonly approximately 6 on average.

*Buds.*—Shape: just before opening elongated, and globular at the apex. Length: approximately 1 cm on average. Diameter approximately 3 mm on average at the widest point.

*Corolla.*—Shape: generally round. Diameter: commonly approximately 2.2 cm on average. Depth: commonly approximately 2.5 cm on average.

*Petals.*—Number: 5 which are fused at the base to form a tube. Shape: obovate. Length: commonly approximately 1.1 cm on average for an upper petal measured from the tube, commonly approximately 1.0 cm on average for a lateral petal measured from the tube, and commonly approximately 1.0 cm on average for a lower petal measured from the tube. Width: commonly approximately 1.1 cm on average for an upper petal, commonly approximately 9.2 mm on average for a lateral petal measured from the tube, and commonly approximately 6 mm on average for a lower petal. Margin: entire. Apex: emarginate. Texture: satiny on upper and under surfaces and velvety in appearance. Color: when first open near Purple Group 78A on the upper surface and near Purple Group 78C on the under surface, and when fully open near Purple Group 78B on the upper surface and near Purple Group 78C on the under surface.

*Corolla tube.*—Length: commonly approximately 1.5 cm on average. Diameter: commonly approximately 2 mm on average at the distal and proximal ends.

*Androecium.*—Quantity: 4 per flower. Filament length: commonly approximately 1.7 cm on average. Anther shape: generally ovoid. Anther size: commonly approximately 1 mm on average. Anther color near Yellow-Green Group 150C. Pollen quantity: sparse. Pollen color: near Yellow-Green Group 150D.

*Gyneocium.*—Quantity: 1 per flower. Style length: commonly approximately 1.7 cm on average. Style color: near Yellow-Green Group 143A. Stigma shape: biparted. Stigma size: commonly less than 1 mm. Stigma color: near Green Group 144A. Ovary size: commonly approximately 1 mm. Ovary color: near Yellow-Green Group 144A.

*Calyx.*—Shape: tubular with 5 acute tips. Length: commonly approximately 1.2 cm on average. Width: commonly approximately 2 mm on average. Texture: densely pubescent with a mixture of glandular and non-glandular hairs. Gland color: substantially colorless.

*Stipules.*—Shape: lanceolate. Length: commonly approximately 7 mm on average. Width: commonly approximately 4 mm on average at the base. Apex: acuminate. Texture: densely pubescent with a mixture of glandular and non-glandular hairs. Color commonly between Green Group 143A and 143B.

*Peduncle.*—Bearing: generally erect. Strength: moderately strong. Length: commonly approximately 4 cm on average. Diameter: commonly approximately 2 mm on average. Texture: densely pubescent with a mixture of glandular and non-glandular hairs.

Development:

*Vegetation.*—Moderately vigorous.

*Blooming.*—Substantially continuous from spring through the fall when grown outdoors.

*Disease resistance.*—No special resistance to diseases common to *Verbena* has been observed during observations to date.

*Pest resistance.*—No special resistance to pests common to *Verbena* has been observed during observations to date.

*Hardiness.*—During observations to date has been found hardy to U.S.D.A. Hardiness Zone No. 6 with some hardiness in Zone No. 5 when protection is provided.

Plants of the 'Radverb' cultivar have not been observed under all possible environmental conditions to date. Accordingly, it is possible that the phenotypic expression may vary somewhat with changes in light intensity and duration, cultural practices, and other environmental conditions without variance of the genotype.

We claim:

1. A new and distinct *Verbena* plant characterized by the following combination of characteristics:

(a) forms in abundance over an extended period of time attractive fragrant blossoms that are purple in coloration, (b) exhibits a moderately vigorous trailing and spreading growth habit, (c) forms attractive medium green foliage that contrasts nicely with the blossom coloration, (d) displays good cold hardiness, and (e) is well suited for growing as attractive ornamentation; substantially as illustrated and described.

* * * * *